(12) United States Patent
Edin

(10) Patent No.: US 8,043,359 B2
(45) Date of Patent: Oct. 25, 2011

(54) MEDICAL DEVICES HAVING SUPERHYDROPHOBIC SURFACES

(75) Inventor: Mark Edin, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 186 days.

(21) Appl. No.: 12/490,042

(22) Filed: Jun. 23, 2009

(65) Prior Publication Data

US 2009/0326639 A1   Dec. 31, 2009

Related U.S. Application Data

(60) Provisional application No. 61/075,549, filed on Jun. 25, 2008.

(51) Int. Cl.
  *A61F 2/06* (2006.01)
  *A61L 27/40* (2006.01)

(52) U.S. Cl. ........................ 623/1.15; 424/426

(58) Field of Classification Search ........ 623/1.11–1.48; 424/426
See application file for complete search history.

(56) References Cited

U.S. PATENT DOCUMENTS

| | | | |
|---|---|---|---|
| 5,306,286 A * | 4/1994 | Stack et al. | 623/1.12 |
| 5,618,299 A | 4/1997 | Khosravi et al. | |
| 5,700,286 A * | 12/1997 | Tartaglia et al. | 623/1.15 |
| 5,733,328 A | 3/1998 | Fordenbacher | |
| 5,824,038 A | 10/1998 | Wall et al. | |
| 6,156,062 A * | 12/2000 | McGuinness | 623/1.22 |
| 6,224,626 B1 | 5/2001 | Steinke | |
| 7,258,731 B2 * | 8/2007 | D'Urso et al. | 106/2 |
| 7,391,018 B2 * | 6/2008 | Niu et al. | 250/288 |
| 7,722,662 B2 * | 5/2010 | Steinke et al. | 623/1.16 |
| 7,763,065 B2 * | 7/2010 | Schmid et al. | 623/1.15 |
| 7,803,574 B2 * | 9/2010 | Desai et al. | 435/41 |
| 2001/0044651 A1 | 11/2001 | Steinke et al. | |
| 2004/0093076 A1 | 5/2004 | White et al. | |
| 2005/0038498 A1 | 2/2005 | Dubrow et al. | |
| 2005/0113936 A1 * | 5/2005 | Brustad et al. | 623/23.71 |
| 2005/0221072 A1 | 10/2005 | Dubrow et al. | |
| 2006/0029808 A1 | 2/2006 | Zhai et al. | |
| 2006/0085063 A1 | 4/2006 | Shastri et al. | |
| 2006/0240218 A1 * | 10/2006 | Parce | 428/98 |
| 2007/0005024 A1 | 1/2007 | Weber et al. | |
| 2007/0067020 A1 | 3/2007 | Rea et al. | |
| 2007/0225800 A1 | 9/2007 | Sahatjian et al. | |
| 2008/0226694 A1 * | 9/2008 | Gelbart et al. | 424/426 |
| 2008/0248263 A1 * | 10/2008 | Kobrin | 428/195.1 |

(Continued)

FOREIGN PATENT DOCUMENTS

EP  1574180 A  9/2005

(Continued)

OTHER PUBLICATIONS

S. Singh et al., "Drying transition of confined water", Nature, 442, 2006, p. 526.

(Continued)

*Primary Examiner* — Suzette J Gherbi
(74) *Attorney, Agent, or Firm* — Mayer & Williams PC; David B. Bonham; Keum J. Park

(57) ABSTRACT

According to an aspect of the invention, medical devices are provided, which have at least two superhydrophobic surface regions which engage one another when the medical device is deployed in vivo.

17 Claims, 3 Drawing Sheets

U.S. PATENT DOCUMENTS

| | | | |
|---|---|---|---|
| 2009/0124034 A1* | 5/2009 | Niu et al. | 438/49 |
| 2009/0281250 A1* | 11/2009 | DeSimone et al. | 525/418 |
| 2010/0086604 A1* | 4/2010 | Stellacci et al. | 424/489 |
| 2010/0285972 A1* | 11/2010 | Dubrow et al. | 506/7 |

FOREIGN PATENT DOCUMENTS

| | | |
|---|---|---|
| WO | 9853765 A | 12/1998 |
| WO | 2006045555 A | 5/2006 |

OTHER PUBLICATIONS

Sandia National Laboratories, News Release, Aug. 2, 2006, "Sandia researchers solve mystery of attractive surfaces," 2 pp.

P. Favia et al., "Deposition of super-hydrophobic fluorocarbon coatings in modulated RF glow discharges," Surface and Coatings Technology, 169-170 (2003) 609-612.

A.V. Rao et al., "Comparative studies on the surface chemical modification of silica aerogels based on various organosilane compounds of the type RnSiX4-n," Journal of Non-Crystalline Solids 350 (2004) 216-223.

K. K. S. Lau et al., "Superhydrophobic Carbon Nanotube Forests" Nanoletters 3, 1701 (2003).

L. Zhai et al., "Stable Superhydrophobic Coatings from Polyelectrolyte Multilayers," Nano Letters, 2004, vol. 4, No. 7, 1349-53.

* cited by examiner

MEDICAL DEVICES HAVING SUPERHYDROPHOBIC SURFACES

RELATED APPLICATIONS

This application claims priority from U.S. provisional application 61/075,549, filed Jun. 25, 2008, which is incorporated by reference herein in its entirety.

TECHNICAL FIELD

The present invention relates to medical devices, and more particularly to medical devices having hydrophobic surfaces.

BACKGROUND

Stents are generally tubular devices that are used to support a segment of a blood vessel or other anatomical lumen so as to maintain its patency. Stents are useful, for example, in the treatment of atherosclerotic stenoses in blood vessels, maintaining blood perfusion to downstream tissue after opening of a flow restriction (e.g., via balloon angioplasty). Various types of stent designs have been developed for treating diseases of blood vessels and other tubular structures inside the body. The currently available stents can be classified into two broad categories: affirmatively-expandable and self-expanding.

An affirmatively-expandable stent may be collapsed down on a dilatation catheter while in a radially contracted state, for example, a stent may be collapsed down onto a folded balloon on the end of a balloon dilatation catheter. The stent maintains this collapsed configuration until it is expanded by the dilatation catheter. For example, when the stent has been properly positioned within the lumen, the dilatation catheter may be actuated (e.g., by inflating a balloon within the stent to an appropriate size), expanding the stent to the desired diameter. The catheter is then returned to a contracted state (e.g., by balloon deflation), and the catheter is withdrawn, leaving the expanded stent in place within the lumen. The stent typically remains in its expanded state because of the plastic deformation that was imparted to its structural elements during expansion.

An affirmatively-expandable stent has many attractive attributes. For example, its diameter and outward force against the vessel wall can be adjusted, for instance, by controlling the inflation pressure of the balloon. Affirmatively-expandable stents, however, can also present certain disadvantages. For example, one disadvantage of certain stent designs is that there is some degree of elastic recoil after expansion. Such elastic recoil usually means that there is a reduction in diameter after the balloon is deflated. The degree of reduction in diameter is related, for example, to material selection, structural design, and degree of inward force from the vessel wall. Balloon-expandable stents are known that employ ratcheting or latching means for retaining the expanded configuration. For one example of such a stent, see, e.g., Pub. No. U.S. 2004/0093076 to White et al.

SUMMARY OF THE INVENTION

According to an aspect of the invention, medical devices are provided, which have at least two superhydrophobic surface regions which engage one another when the medical device is deployed in vivo.

An advantage of such devices is that the engaged superhydrophobic surface regions help maintain the device in an as-deployed state.

These and other aspects, embodiments and advantages of the present invention will become immediately apparent to those of ordinary skill in the art upon review of the Detailed Description and any claims to follow.

DETAILED DESCRIPTION OF THE INVENTION

Figures 1A, 1B:
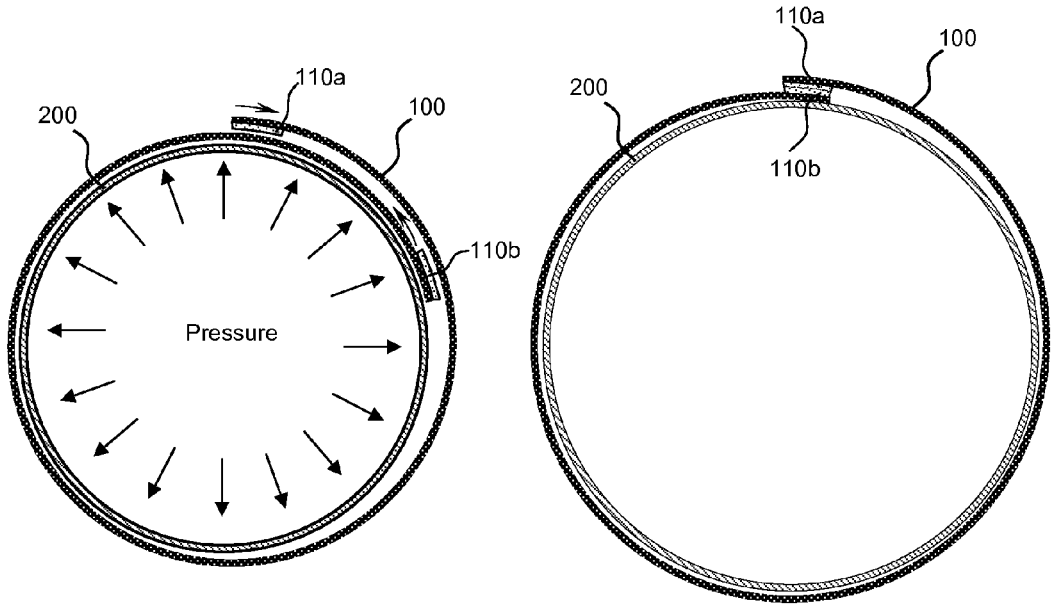
FIG. 1A is a schematic cross-sectional view of an assembly that includes a stent body and a dilatation balloon, in accordance with an embodiment of the present invention.
FIG. 1B is a schematic cross-sectional view of the assembly of FIG. 1A, after inflation of the balloon.

According to an aspect of the present invention, medical devices are provided which have two or more superhydrophobic surface regions (sometimes referred to as superhydrophobic surfaces) which engage one another in vivo.

For example, in some embodiments, stents are provided, which have at least first and second superhydrophobic surface regions which engage one another upon expansion of the stent in vivo. Stents for use in the present invention include vascular stents (e.g., coronary vascular stents, peripheral vascular stents, cerebral stents, etc.), urinary stents (e.g., urethral stents, ureteral stents, etc.), tracheal stents and gastrointestinal stents (e.g., esophageal stents, biliary stents, enteral stents, colorectal stents, etc.), among others.

For purposes of the present invention, a superhydrophobic surface region is one that displays dynamic (receding and/or advancing) water contact angles of 145° or above (e.g., ranging from 145° to 150° to 155° to 160° to 165° to 170° to 175° to 180°). In particularly beneficial embodiments, both the receding and the advancing water contact angles are 145° or above.

The Wilhelmy plate technique is a suitable technique for measuring the dynamic contact angles for various surfaces, including the superhydrophobic surfaces that are formed in conjunction with the present invention. This technique is performed with a solid sample, typically a rectangular plate or some other regular shape such as a cube, round rod, square rod, tube, etc. To the extent that the medical device of interest is not of sufficiently regular geometry to allow its surface to be tested directly using this technique, a sample of regular geometry, which is provided with a surface using the same materials and processes used to provide the medical device surface, may be tested so as to infer the dynamic contact angles of the device.

The Wilhelmy plate technique is performed using a tensiometer. The solid sample is immersed into and withdrawn out of a liquid (i.e., water) while simultaneously measuring the force acting on the solid sample. Advancing and receding contact angles can then be determined from the obtained force curve using well known calculations. The advancing contact angle is the contact angle that is measured as the sample is immersed in the liquid, whereas the receding contact angle is the contact angle that is measured as the sample is removed from the liquid.

Certain plants in nature, including the lotus leaf, exhibit the unusual wetting characteristic of superhydrophobicity. The lotus leaf accomplishes this effect through the use of a surface topography that presents two different length scales to the outside environment. The surface of the lotus leaf, for example, is textured with 3-10 micron-sized hills and valleys that are decorated with nanometer-size particles of a hydrophobic wax-like material. It has been suggested that the hills and valleys ensure that the surface contact area available to water is very low, whereas the hydrophobic nanoparticles prevent penetration of water into the valleys. Whatever the exact mechanism, the net result is that water does not wet the surface and therefore forms nearly spherical water droplets. See, e.g., Pub. No. U.S. 2006/0029808 to Zhai et al.

A typical way of enhancing the hydrophobicity of an object is to employ surface materials with low surface energy, such as fluorocarbon polymers. However, such materials do not ordinarily provide superhydrophobic water contact angles (fluorocarbon polymers ordinarily exhibiting water contact angles that are only as great as about 120° or so). Nevertheless, as indicated above, surfaces with substantially greater water contact angles exist in nature. Moreover, man-made surfaces having superhydrophobic water contact angles also been created. In addition to having low surface energy (inherently hydrophobic) materials present, these surfaces generally possess microscale and/or nanoscale surface texturing (see, e.g., the description of the lotus leaf supra and the description of various synthetic superhydrophobic materials infra).

Superhydrophobic surface regions are known to bind together spontaneously in the presence of water. Without wishing to be bound by theory, it has been reported that this behavior is based on very-long-range hydrophobic attractive forces (e.g., up to 3.5 microns), which are due to evaporation, or "cavitation." Cavitation is a first-order phase transition characterized by a sudden, strong attractive force and by the appearance of a vapor bridge. For further information, see, e.g., S. Singh et al., *Nature*, 442, 2006, p. 526.

In the present invention, such attractive forces between superhydrophobic surfaces are employed to (reversibly) bind adjacent medical device surfaces, thereby maintaining the position of the surfaces with respect to one another. For example, in the case of an affirmatively-expandable stent, bringing binding two or more surfaces in this fashion can help to offset the effects of elastic recoil after expansion.

Various embodiments of the invention pertain to stents, although as indicated above, the invention is applicable to devices other than stents. In these embodiments, the stent typically comprises a substantially two-dimensional element which has a curvature that forms all or a portion of a tubular structure. For example, a sheet-like element may extend partially or completely around an axis to form a tubular structure or a portion thereof, a ribbon-like element may extend partially or completely around an axis to form a ring-shaped structure or a portion thereof, a ribbon-like element may extend along the length of an axis in the form of a helix, and so forth.

As used herein, a "substantially two-dimensional element" is one whose thickness is much less than its length and its width, with thicknesses typically being less than ⅕ the width and the length, more typically less than 1/10 the width and the length. As indicated above, examples include sheet-like element and ribbon-like elements, among others.

In certain of these embodiments, the medical device may be a stent that comprises a sheet of material that is rolled upon itself, with at least one superhydrophobic surface region positioned on one side and at one end of the of the sheet and at least one superhydrophobic surface region positioned on the opposite side and at the opposite end of the sheet.

For instance, FIG. 1A is a schematic cross-sectional view of an assembly that includes a rolled sheet 100, which forms the body of a stent. A first superhydrophobic surface region 110*a* is found on one side and at one end of the sheet 100, and a second superhydrophobic surface region 110*b* is found on the opposite side and at the opposite end of the sheet 100.

Figure 2:
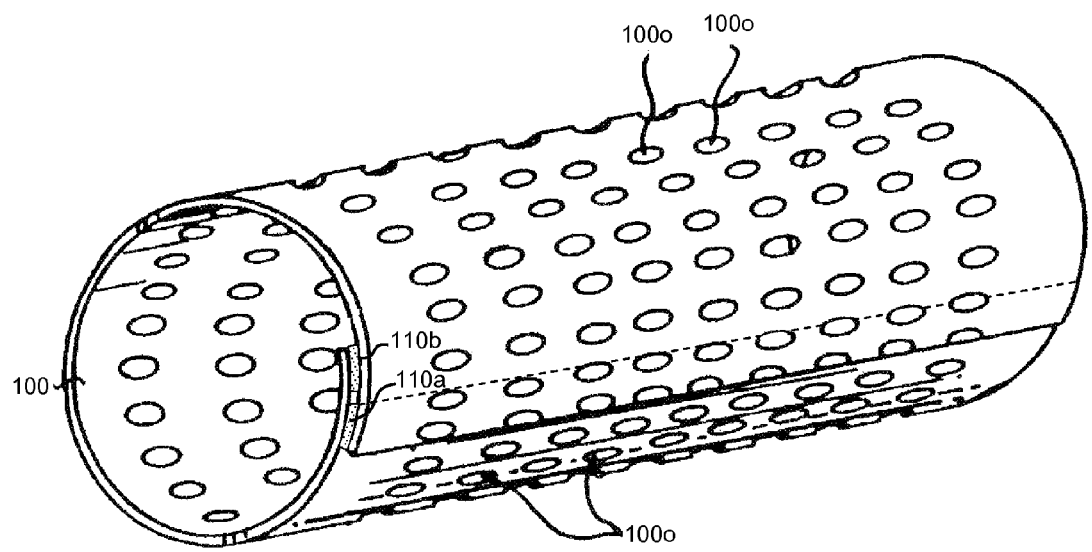
FIG. 2 is a perspective view of a stent like that shown in FIGS. 1A and 1B.

A perspective view of a stent of this type is shown in FIG. 2, in which the rolled sheet 100, first superhydrophobic surface region 110*a*, and second superhydrophobic surface region 110*b* are shown. The dashed line illustrates the fashion by which the first superhydrophobic surface region 110*a* extends along the length of the stent. The rolled sheet 100 includes openings 100*o* as is known in the art.

Returning now to FIG. 1A, a balloon 200 is shown disposed within a lumen that is formed by the rolled sheet 100. The balloon 200 exerts an outward force upon inflation, causing the rolled sheet of FIG. 1A to expand in diameter, bringing the first and second superhydrophobic surface regions 110*a*, 110*b* into contact/engagement with one another as shown in FIG. 1B. The attraction between the superhydrophobic surface regions 110*a*, 110*b* helps maintain the stent in its expanded state. If desired, the stent can be equipped with a limiting mechanism to prevent expansion beyond the position shown in FIG. 1B.

Figure 5:
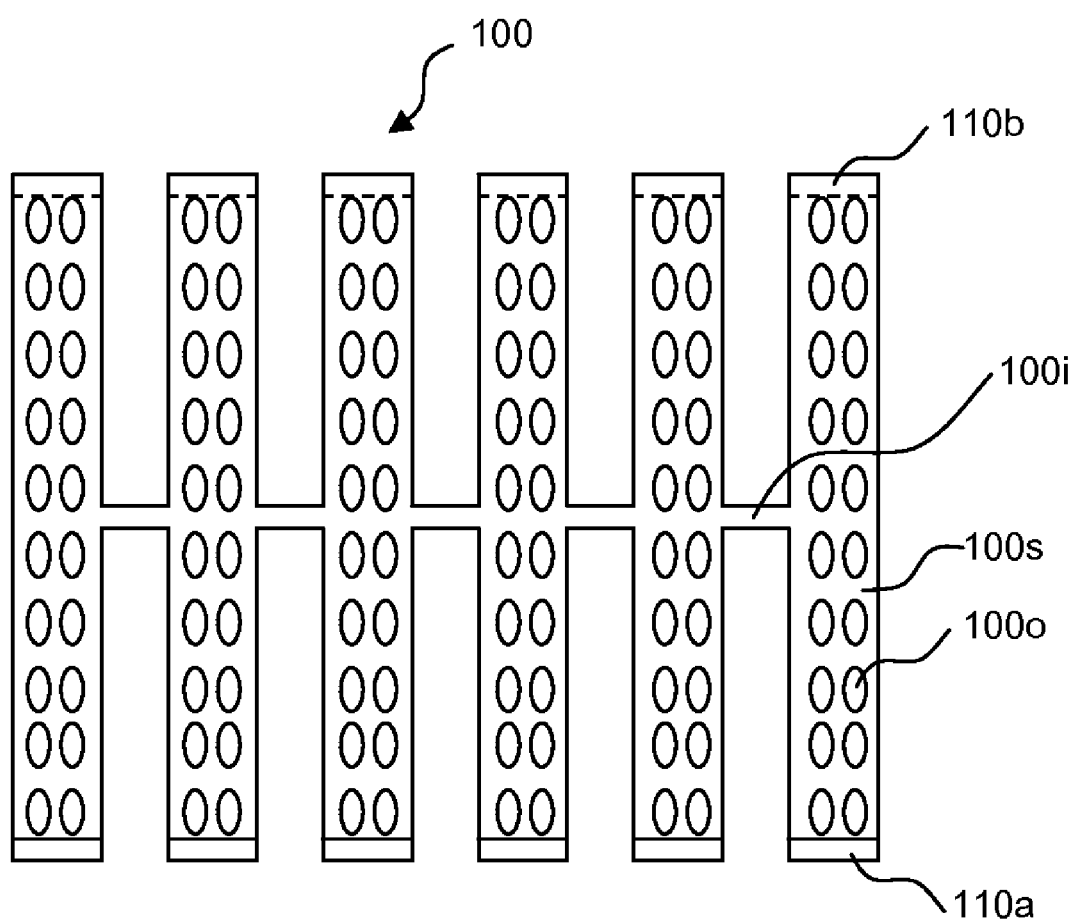
FIG. 5 is a schematic top view of a stent body (in unrolled form), in accordance with another embodiment of the present invention.

Although the stent shown in FIG. 2 is formed from a single rolled element, one can readily envision stents in which multiple rolled elements are employed. For example, FIG. 5 is a top view of an unrolled stent body 100, which includes six sheet sections 100*s*, which can be rolled into circular bands. The six sheet sections 100*s* are attached to one another by five narrow interconnect sections 100*i*. As above, the sheet sections 100*s* include openings 100*o*. Moreover, each sheet section 100*s* includes a first superhydrophobic surface region 110*a* on one side and at one end of the sheet section 100*s*, and a second superhydrophobic surface region 110*b* is found on the opposite side and at the opposite end of the sheet section 100*s*.

Figure 3:
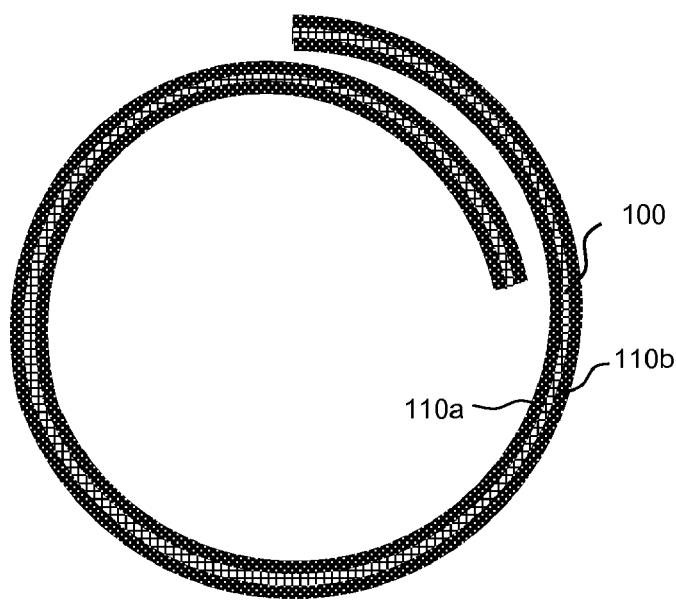
FIG. 3 is a schematic end view of a stent body, in accordance with another embodiment of the present invention.

In the embodiment shown in FIGS. 1A, 1B, 2 and 5, the superhydrophobic surface regions 110*a*, 110*b* interact with one another only at or near the furthest point of expansion. In other embodiments, like that shown in FIG. 3, the first and second superhydrophobic surface regions 110*a*, 110*b* can cover large portions (e.g., more than 25%) of the respective sides of the rolled sheet 100, up to and including the entire respective sides. In these embodiments, the balloon pressure overcomes the sliding friction between the superhydrophobic surface regions 110*a*, 110*b*, as the first and superhydrophobic surface regions 110*a*, 110*b* slide relative to one another during expansion.

Figure 4:
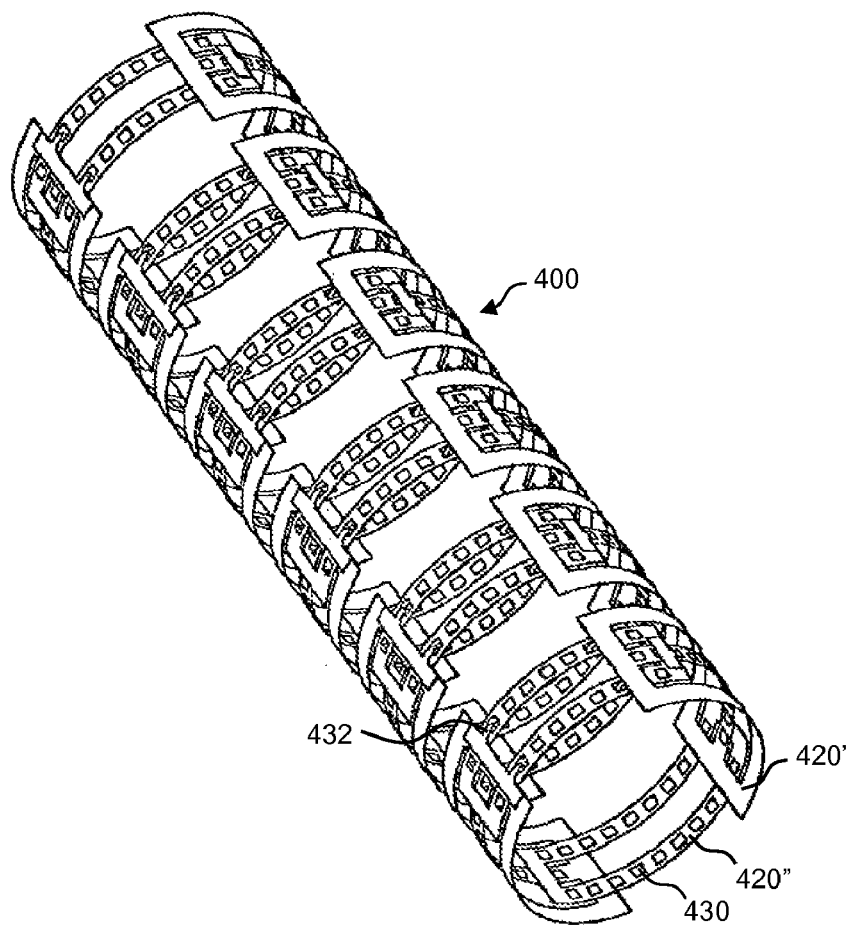
FIG. 4 is a perspective view of a stent in accordance with the prior art.

FIG. 4 is an illustration of a stent 400 which is described in Pub. No. U.S. 2001/0044651 to Steinke et al. The stent is made up of multiple first radial elements 420' and multiple second radial elements 420". The first radial elements 420' are in slidable engagement with the second radial elements 420", such that the diameter of the stent 400 can be expanded. The stent 400 is held in an expanded state by a ratcheting effect that is achieved by the interaction between tabs/teeth 432 that are formed on the first radial elements 420' and stops 430 that are formed in the second radial elements 420".

In accordance with an embodiment of the present invention, a design like that shown in FIG. 4 may be modified to eliminate the tabs/teeth 432 on the first radial elements 420' and the stops 430 in the second radial elements 420". Moreover, at least those surface regions of the first and second radial elements 420', 420" that contact one another upon expansion may be rendered superhydrophobic.

As indicated above, in addition to being formed using a low surface energy material (e.g., an inherently hydrophobic material), superhydrophobic surfaces typically have an associated surface roughness. Examples of low surface energy materials include fluorocarbon materials (i.e., materials containing molecules having C—F bonds), for instance, fluorocarbon homopolymers and copolymers such as polytetrafluoroethylene (PTFE), fluorinated ethylene propylene (FEP), ethylene tetrafluoroethylene (ETFE), ethylene chloro-trifluoroethylene (ECTFE), perfluoro-alkoxyalkane (PFA), poly (chloro-trifluoro-ethylene) (CTFE), perfluoro-alkoxyalkane (PFA), and poly(vinylidene fluoride) (PVDF), among many others.

Various methods for providing superhydrophobic surface regions are known, several of which are described in Pub No. U.S. 2007/0005024 to Weber et al., which is hereby incorporated by reference.

Such methods include methods in which an inherently hydrophobic surface material (e.g., a fluorocarbon material, such as a fluorocarbon polymer) is textured to render it superhydrophobic (e.g., using laser ablation techniques, plasma etching techniques, or lithographic techniques in which a material is etched through apertures in a patterned mask). The hydrophobic surface material may correspond to a substrate material or to one or more layers disposed over a substrate material.

Such methods further include methods in which one or more layers of hydrophobic material (e.g., a fluorocarbon material, such as a fluorocarbon polymer) is/are provided over a textured surface. The textured surface may correspond, for example, to a textured substrate material or to one or more layers of textured material disposed over a substrate material, for instance, one or more layers that comprise a sol-gel material or a particulate material (e.g., carbon nanotubes). For instance, a fluorocarbon polymer coating may be deposited over a textured surface by chemical vapor deposition or glow discharge deposition.

In some embodiments, layer-by-layer processes (in which multiple layers of alternating charge are deposited over underlying substrates) may be employed to produce superhydrophobic surface regions. For example, the layers of alternating charge may comprise a negatively charged polyelectrolyte-containing layer, a positively charged polyelectrolyte-containing layer, and a charged particle layer. Polyelectrolytes which can confer hydrophobicity include fluorinated polyelectrolytes.

Specific techniques for forming superhydrophobic coatings over underlying substrates are described, for example, in P. Favia et al., "Deposition of super-hydrophobic fluorocarbon coatings in modulated RF glow discharges," *Surface and Coatings Technology*, 169-170 (2003) 609-612 (who report deposited coatings with water contact angle values of 150-165°, characterized by a high degree of fluorination and having ribbon-like randomly distributed surface microstructures that have feature sizes on the order of a micron), A. V. Rao et al., "Comparative studies on the surface chemical modification of silica aerogels based on various organosilane compounds of the type $R_nSiX_{4-n}$," *Journal of Non-Crystalline Solids* 350 (2004) 216-223 (who report chemically modified hydrophobic silica aerogels with contact angles as high as 175°), K. K. S. Lau et al., "Superhydrophobic Carbon Nanotube Forests" *Nanoletters* 3, 1701 (2003) (who report a vertically aligned carbon nanotube "forest," covered by a thin, conformal polytetrafluoroethylene layer, which displays advancing and receding contact angles of 170° and 160°, respectively), L. Zhai et al., "Stable Superhydrophobic Coatings from Polyelectrolyte Multilayers," *Nano Letters*, 2004, Vol. 4, No. 7, 1349-53 (who report surfaces having advancing and receding water contact angles in excess of 160°, formed by first creating a honeycomb-like polyelectrolyte multilayer surface having pores on the order of 10 microns, which is subsequently overcoated with a layer of negatively charged 50 nm silica nanoparticles, followed by chemical vapor deposition of a semifluorinated silane layer).

Using techniques such as those above, a wide range of substrate materials may be provided with superhydrophobic surface regions, suitable examples of which may be selected, for example, from the various substrate materials set forth below. It is also noted that certain of the above techniques are particularly well adapted to forming superhydrophobic surfaces over the interior surfaces of substrate materials, including sol-gel layer-by-layer techniques, layer-by-layer techniques, and CVD techniques.

For further information regarding the formation of superhydrophobic surfaces, see, e.g., Pub No. U.S. 2007/0005024 and the references cited therein.

Substrate materials for use in the invention vary widely and may be selected from (a) organic materials (e.g., materials containing 50 wt % or more organic species) such as polymeric materials and (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., biostable metals such as gold, platinum, palladium, iridium, osmium, rhodium, titanium, tantalum, tungsten, niobium and ruthenium, and bioresorbable metals such as magnesium and iron), metal alloys comprising iron and chromium (e.g., stainless steels, including platinum-enriched radiopaque stainless steel), niobium alloys, alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and bioabsorbable metal alloys (e.g., alloys of magnesium, zinc or iron), for example, alloys containing two or more of the following: Mg, Zn, Fe, Ce, Ca, Zr and Li, among others.

Examples of polymeric substrate materials include various biostable and bioresorbable polymers known in the medical device art. Examples include those substrate materials described in Pub No. U.S. 2007/0005024.

Although various embodiments of the invention are specifically illustrated and described herein, it will be appreciated that modifications and variations of the present invention are covered by the above teachings without departing from the spirit and intended scope of the invention.

The invention claimed is:

1. A stent comprising a plurality of superhydrophobic surface regions which engage one another upon stent expansion in vivo, wherein the stent comprises a substantially two-dimensional stent element, which has a curvature and which forms all or a portion of a tubular structure, wherein the substantially two-dimensional stent element comprises a first superhydrophobic surface region on a first side and a second superhydrophobic surface region on a second opposite side, and wherein the first superhydrophobic surface region corresponds to a fraction of the first side and the second superhydrophobic surface region corresponds to a fraction of the second side.

2. The medical device of claim 1, wherein the stent is a coronary vascular stent.

3. The medical device of claim 1, wherein the substantially two-dimensional stent element contains one or more perforations.

4. A stent comprising first and second superhydrophobic surface regions which engage one another upon stent expansion in vivo, wherein the stent comprises a substantially two-dimensional stent element, which has a curvature and which forms all or a portion of a tubular structure, wherein the substantially two-dimensional stent element comprises said first superhydrophobic surface region on a first side and said second superhydrophobic surface region on a second opposite side.

5. The medical device of claim 4, wherein the wherein the first superhydrophobic surface region corresponds to the entire first side and the second superhydrophobic surface region corresponds to the entire second side.

6. The medical device of claim 1, wherein the stent is selected from vascular stents, urinary stents and gastrointestinal stents.

7. The medical device of claim 1, wherein the first superhydrophobic surface region is positioned at one end of the substantially two-dimensional stent element and the second superhydrophobic surface region is positioned at the opposite end of the substantially two-dimensional stent element.

8. The medical device of claim 1, comprising multiple substantially two-dimensional elements.

9. The medical device of claim 1, wherein the substantially two-dimensional element is a sheet-like element.

10. The medical device of claim 1, wherein the substantially two-dimensional element is a ribbon-like element.

11. The medical device of claim 1, wherein the substantially two-dimensional element is rolled completely or partially around an axis in the form of a complete or partial ring or a complete or partial tube.

12. The medical device of claim 1, wherein the substantially two-dimensional element is a ribbon-like element that is rolled along an axis in the form of a helix.

13. The medical device of claim 1, wherein each of said superhydrophobic surface regions corresponds to a textured fluorocarbon material surface.

14. The medical device of claim 1, wherein said superhydrophobic surface regions correspond to a coating that is formed over an underlying substrate.

15. The medical device of claim 14, wherein said coating is a multilayer coating.

16. The medical device of claim 14, wherein said coating comprises a fluorocarbon polymer layer.

17. The medical device of claim 16, wherein said fluorocarbon polymer layer is provided over a textured surface.

* * * * *